US012605511B2

(12) United States Patent
Wu et al.

(10) Patent No.: US 12,605,511 B2
(45) Date of Patent: Apr. 21, 2026

(54) MEDICAL PRECISE DOSE SYRINGE FOR BOTULINUM TOXIN

(71) Applicant: Qingdao Diao Medical Technology Co., Ltd., Qingdao (CN)

(72) Inventors: Wenyu Wu, Shanghai (CN); Qin Li, Chengdu (CN); Jufang Zhang, Hangzhou (CN); Lin Gao, Xi'an (CN); Yuanhong Li, Shenyang (CN); Xueli Li, Zhengzhou (CN); Miao Li, Shenyang (CN); Xiaodong Zhao, Harbin (CN)

(73) Assignee: Qingdao Diao Medical Technology Co., Ltd., Qingdao (CN)

( * ) Notice: Subject to any disclaimer, the term of this patent is extended or adjusted under 35 U.S.C. 154(b) by 19 days.

(21) Appl. No.: 18/757,157

(22) Filed: Jun. 27, 2024

(65) Prior Publication Data

US 2026/0000840 A1      Jan. 1, 2026

(51) Int. Cl.
     *A61M 5/315*          (2006.01)
(52) U.S. Cl.
     CPC ............................... *A61M 5/31555* (2013.01)
(58) Field of Classification Search
     CPC .......... A61M 5/31555; A61M 5/31556; A61M 5/3156; A61M 5/31563; A61M 5/31568; A61M 5/31566

USPC .................................................. 604/207–210
See application file for complete search history.

(56)                References Cited

U.S. PATENT DOCUMENTS 2,707,954 A * 5/1955 Kas, Sr. .............. A61M 5/3158
                                                    604/210
2007/0265579 A1* 11/2007 Kleyman ................. A61C 5/62
                                                    604/207

* cited by examiner

*Primary Examiner* — Philip E Stimpert
(74) *Attorney, Agent, or Firm* — JEEN IP LAW, LLC

(57)                ABSTRACT

A precise dose syringe for medical botulinum toxin is provided, which includes a syringe and a plunger handle. Multiple arc-shaped grooves are respectively provided on both sides of the plunger handle, and a scale line is processed on the front side of the plunger handle. A reminder mechanism and a quantitative mechanism are sleeved on the outer side of the plunger handle. The indicator arrow is located in front of the plunger handle, and the I-shaped block is connected to a thumb screw. The front side of the thumb screw is fixedly connected to a contact block, and the front side of the contact block is in contact with a back side of the plunger handle. The quantitative mechanism can make the injection dose of the syringe precise and controllable, while the reminder mechanism can remind doctors of the real-time injection amount during botulinum toxin injection.

7 Claims, 7 Drawing Sheets

4

6

5

7

8

1

2

6

5

4

3

MEDICAL PRECISE DOSE SYRINGE FOR BOTULINUM TOXIN

TECHNICAL FIELD

The present disclosure relates to the technical field of syringe, in particular to a medical precise dose syringe for botulinum toxin.

BACKGROUND

Botulinum toxin is a toxin produced by *Clostridium botulinum*, which is a neurotoxin originally used to treat facial muscle spasms and other muscle movement disorders. It is used to paralyze muscle nerves and achieve the goal of stopping muscle spasms. It was later applied to medical cosmetology. Botulinum toxin can block the nerve impulses between nerves and muscles, so that the over-contracted small muscles can relax, and then achieve the effect of wrinkle removal. Alternatively, it can be used to temporarily paralyze the muscles, so that the muscles atrophy due to loss of function, to achieve the purpose of sculpture lines, which is often referred to as wrinkle and face slimming.

Botulinum toxin injection requires the use of a syringe, and the dosage of botulinum toxin injection needs to be very precise, which is a high requirement for plastic surgeons. Doctors can only improve the accuracy of injection through repeated injection training.

But for young doctors, the technical requirements are high, and they often cannot control the injection volume well, leading to poor postoperative results and unnecessary doctor-patient disputes. Moreover, due to the interference of uncertain factors during the surgical process, it is difficult to avoid situations where the injection volume is inappropriate, resulting in occasional issues with the treatment outcome.

Therefore, in order to solve the above problems, the present disclosure is to provide a medical precise dose syringe for botulinum toxin.

SUMMARY

The present disclosure provides a precise dosage syringe for medical botulinum toxin to solve the above-mentioned technical problems.

In order to solve the above technical problems, a precise dose syringe for medical botulinum toxin is provided by the present disclosure, which includes a barrel, a needle, a plunger, and a plunger handle, wherein the needle is inserted and connected to a tip at an bottom of the barrel, the plunger is located inside the barrel, the plunger handle is fixedly connected to a top of the plunger, and the plunger handle is located inside the barrel and extends to a top of the barrel; a cross-section of the plunger handle is square, a plurality of arc-shaped grooves are provided on both sides of the plunger handle, and a front side of the plunger handle is provided with a scale line; an outer side of the plunger handle is sleeved with a reminder mechanism and a quantitative mechanism, the reminder mechanism is located inside the barrel and extends out of the top of the barrel, and the quantitative mechanism is located above the barrel; the quantitative mechanism includes a U-shaped sleeve block and an I-shaped block, the I-shaped block is located behind the U-shaped sleeve block and extends to an inside of the U-shaped sleeve block, both side of the inside of the U-shaped sleeve block are provided with an insertion slot respectively, the I-shaped block extends to an inside of the insertion slot, the U-shaped sleeve block is sleeved at an outer end of the plunger handle, a top of the U-shaped sleeve block is provided with an indicator arrow, the indicator arrow is located in a front of the plunger handle, a back side of the I-shaped block is connected to a thumb screw through a thread connection, a front side of the thumb screw is fixedly connected to a contact block, and a front side of the contact block is in contact with a back side of the plunger handle.

Preferably, the reminder mechanism includes a first U-shaped seat and a second U-shaped seat, wherein the first U-shaped seat and the second U-shaped seat are respectively sleeved on both sides of the plunger handle, outer sides of the first U-shaped seat and the second U-shaped seat are fixedly connected to a curved rubber block respectively, an outer end of the curved rubber block is in contact with an inner wall of the barrel, an inner wall of the first U-shaped seat and an inner wall of the second U-shaped seat are provided with a first slot respectively, the first slot is fixedly connected with an elastic piece, and a side of the elastic piece near the plunger handle extends to an interior of the adjacent arc-shaped groove.

Preferably, one side of the first U-shaped seat is fixedly connected to two rectangular blocks, one side of the second U-shaped seat is provided with two rectangular slots, the two rectangular blocks are located inside the two rectangular slots, and the first U-shaped seat and the second U-shaped seat are connected in an insertion connection by the rectangular blocks and the rectangular slots.

Preferably, the first U-shaped seat and the second U-shaped seat form a middle-hollow sleeve, and an inner wall of the middle-hollow sleeve does not contact an outer wall of the plunger handle.

Preferably, an outer wall of the curved rubber block is provided with an anti-slip protrusion, and the curved rubber block is provided inside the barrel in an interference fit.

Preferably, a limit block is integrally formed at a top of each curved rubber block, and the quantitative mechanism is located between two limit blocks.

Preferably, the elastic piece is made of metal material.

Preferably, a front side of the I-shaped block is provided with a second slot, and the contact block is located inside the second slot.

Preferably, both sides of the I-shaped block are provided with two limit balls respectively, two limit slots are respectively arranged on both sides of the U-shaped sleeve block, the limit balls are located inside the limit slots, and the U-shaped sleeve block and the I-shaped block are connected in an interference fit.

Compared with related arts, the medical precise dose syringe for botulinum toxin provided by the present disclosure has the following advantageous effects:

1. By inserting a reminder mechanism through interference fit in the syringe, the elastic piece in the reminder mechanism are inserted into the arc-shaped groove on the plunger handle, and as the plunger handle moves, the elastic piece will deform and enter adjacent arc-shaped grooves, and then the shape of elastic piece returns. The spacing between adjacent arc-shaped grooves is fixed, so each movement of the elastic piece represents a fixed dose of botulinum toxin injection, which can be used to remind doctors of the real-time progress of botulinum toxin injection and also facilitate doctors to control the injection speed;

2. By providing a quantitative mechanism on the plunger handle and adjusting the position of the quantitative mechanism according to the scale line on the plunger handle, the maximum movement stroke of the plunger handle can be controlled each time, thereby making the injection dose of botulinum toxin in the syringe precise and controllable, and safer to use;

3. The reminder mechanism and quantitative mechanism can be disassembled and reassembled for use, in order to facilitate recycling and reduce resource waste. BRIEF

Figure 1:
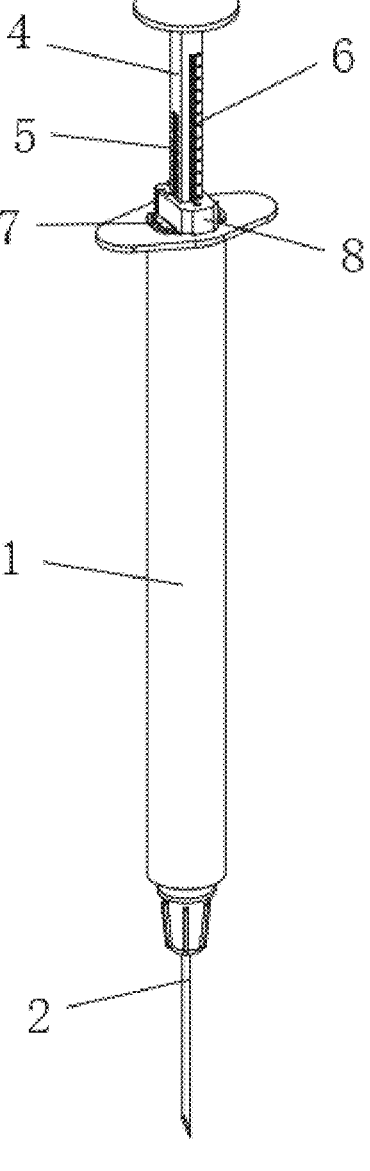
FIG. 1 is a schematic diagram of the overall structure of a medical precise dose syringe for botulinum toxin provided in the present disclosure.

Reference marks in the drawings: 1. barrel, 2. needle, 3. plunger, 4. plunger handle, 5. arc-shaped groove, 6. scale line, 7. reminder mechanism, 8. quantitative mechanism, 9. first U-shaped seat, 10. second U-shaped seat, 11. first slot, 12. elastic piece, 13. rectangular block, 14. rectangular slot, 15. curved rubber block, 16. anti-slip protrusion, 17. limit block, 18. U-shaped sleeve block, 19. I-shaped block, 20. thumb screw, 21. contact block, 22. second slot, 23. indicator arrow, 24. insertion slot, 25. limit slot, 26. limit ball.

DETAILED DESCRIPTION OF THE EMBODIMENTS

Figure 2:
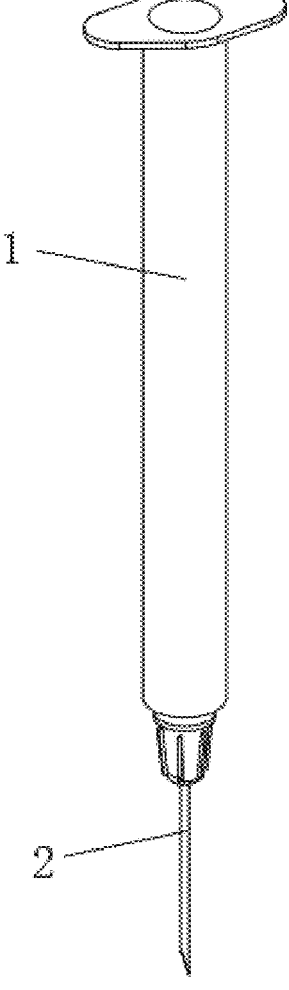
FIG. 2 is a schematic diagram of the syringe structure of the medical precise dose syringe for botulinum toxin provided in the present disclosure.
Figure 3:
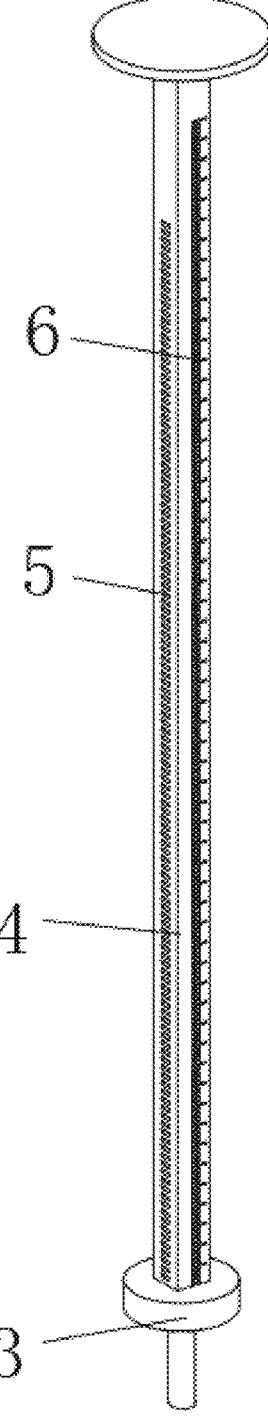
FIG. 3 is a schematic diagram of the plunger handle structure of the medical precise dose syringe for botulinum toxin provided in the present disclosure.
Figure 4:
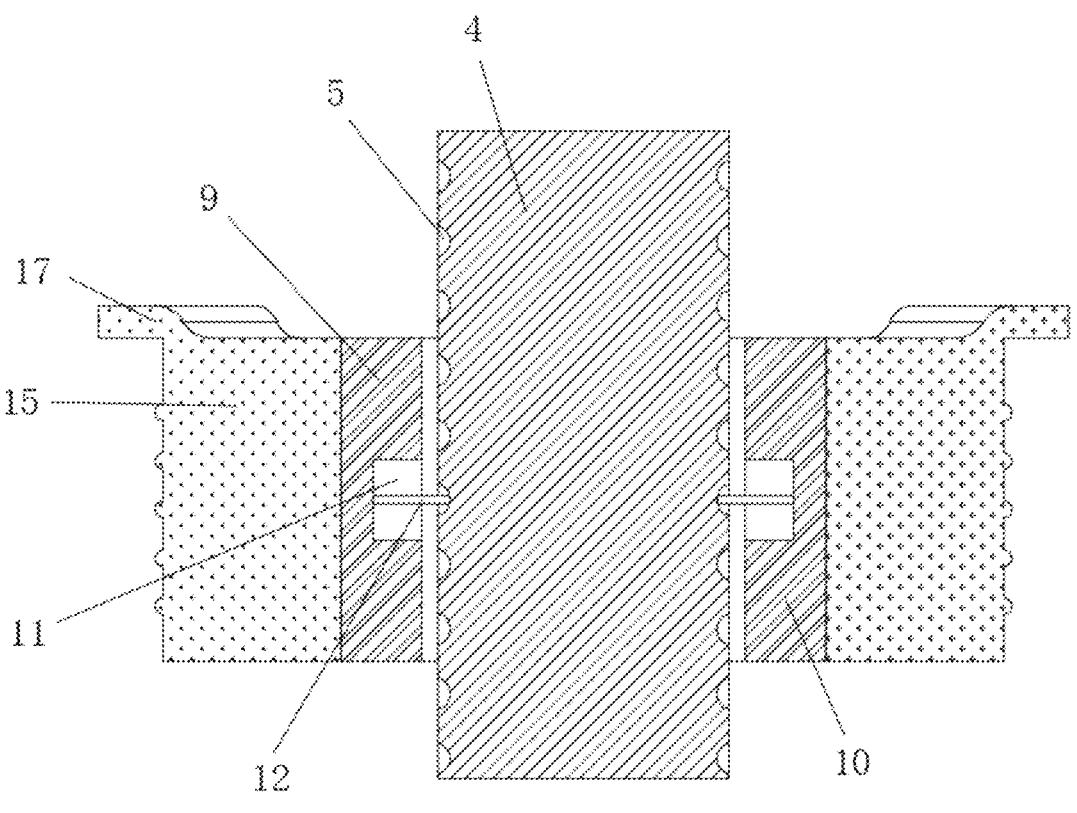
FIG. 4 is the main sectional view of the reminder mechanism of the medical precise dose syringe for botulinum toxin provided in the present disclosure.
Figure 5:
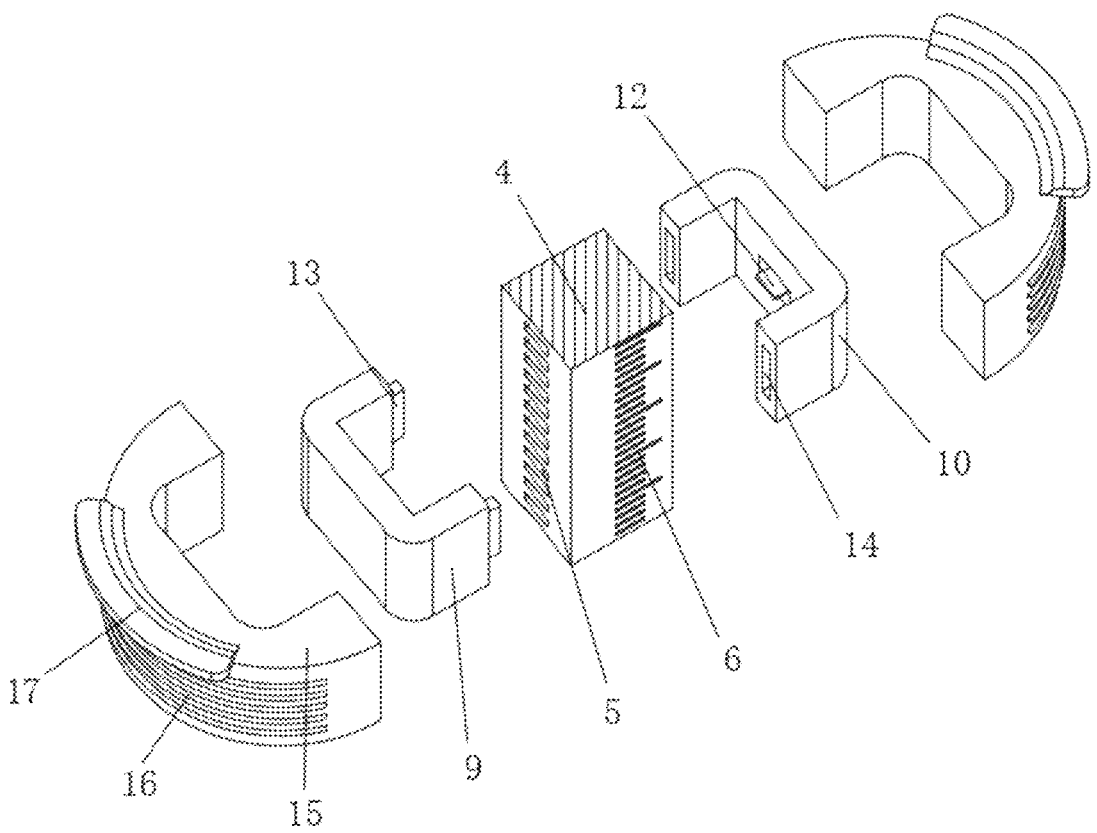
FIG. 5 is an exploded view of the reminder mechanism of the medical precise dose syringe for botulinum toxin provided in the present disclosure.
Figure 6:
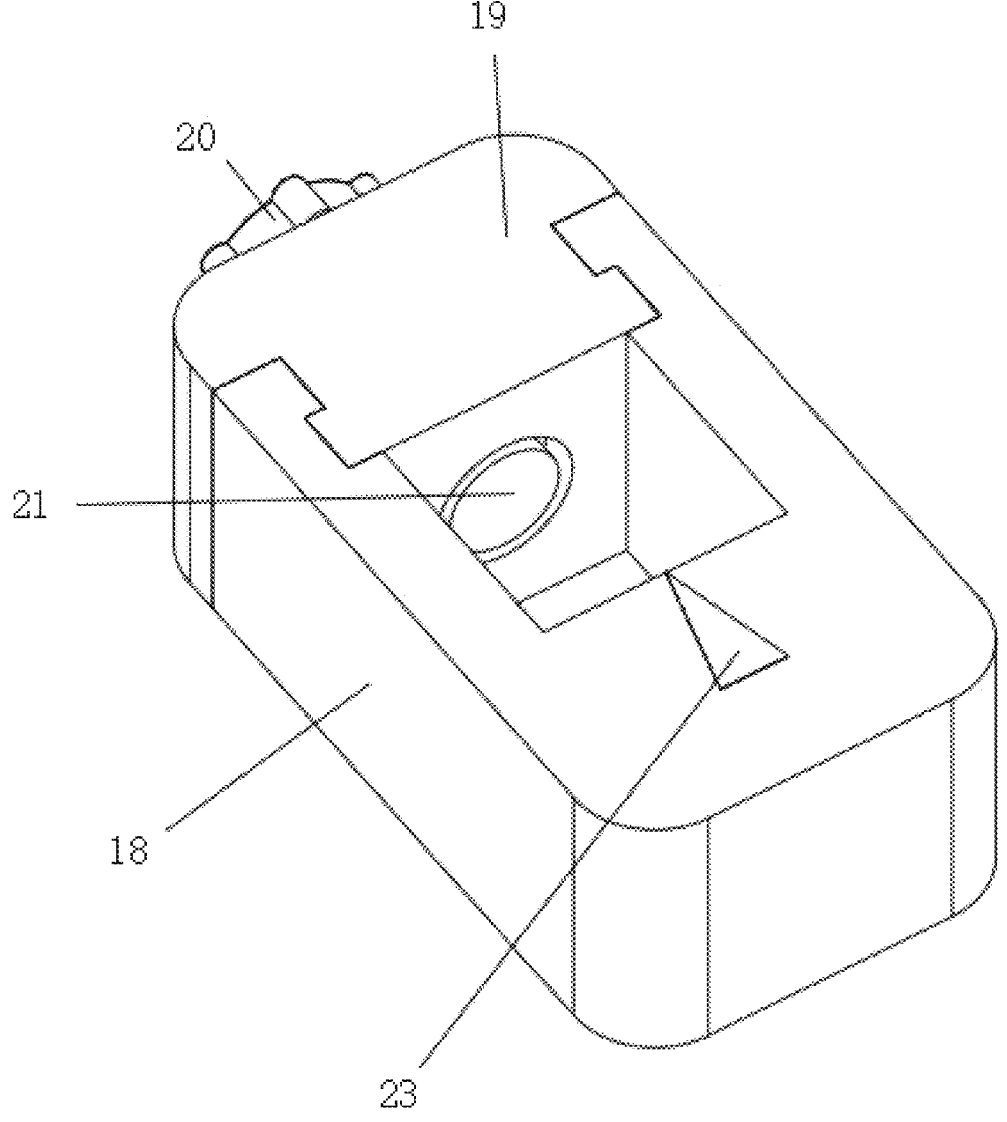
FIG. 6 is a schematic diagram of the quantitative mechanism structure of the medical precise dose syringe for botulinum toxin provided in the present disclosure.
Figure 7:
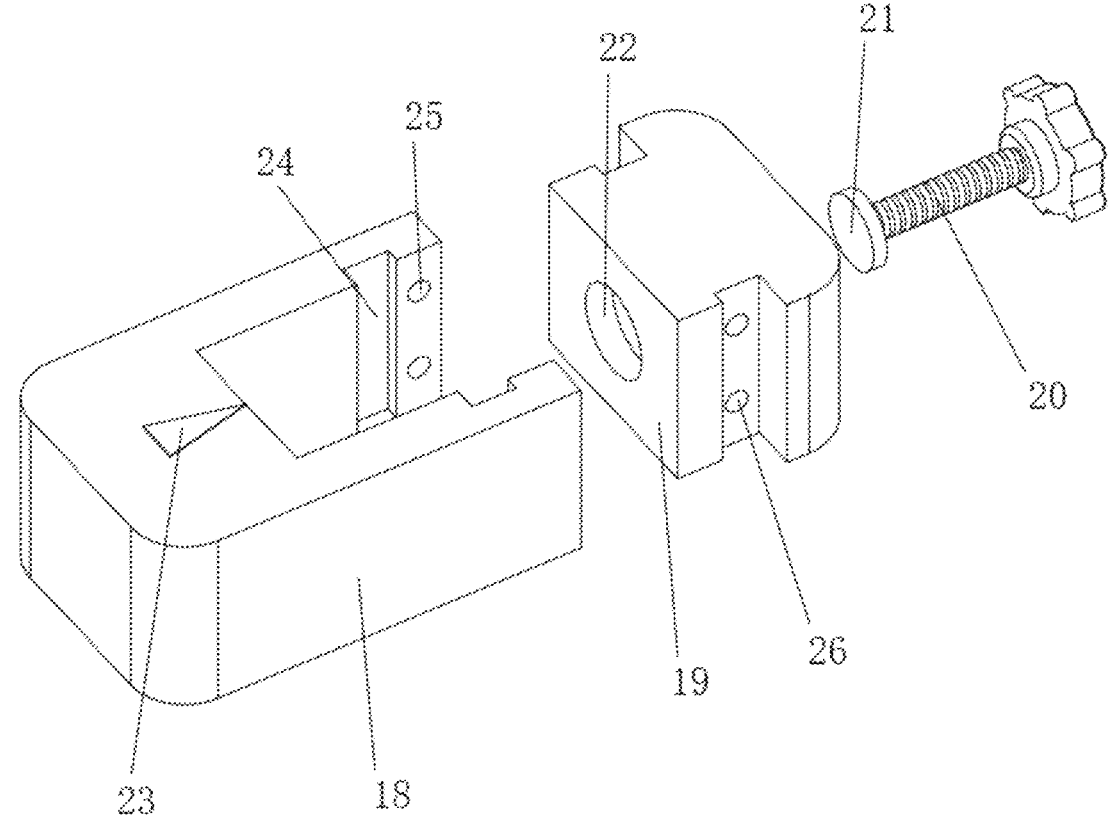
FIG. 7 is an exploded view of the quantitative mechanism of medical precise dose syringe for botulinum toxin provided in the present invention.

In this embodiment, as shown in FIG. 1-FIG. 7, a precise dose syringe for medical botulinum toxin is provided, which includes a barrel 1, a needle 2, a plunger 3, and a plunger handle 4. The needle 2 is inserted and connected to a tip at the bottom of the barrel 1, the plunger 3 is located inside the barrel 1, the plunger handle 4 is fixedly connected to the top of the plunger 3, and the plunger handle 4 is located inside the barrel 1 and extends to the top of the barrel 1. The cross-section of the plunger handle 4 is square, a plurality of arc-shaped grooves 5 are provided on both sides of the plunger handle 4, and the front side of the plunger handle 4 is provided with a scale line 6. The outer side of the plunger handle 4 is sleeved with a reminder mechanism 7 and a quantitative mechanism 8, the reminder mechanism 7 is located inside the barrel 1 and extends out of the top of the barrel 1, and the quantitative mechanism 8 is located above the barrel 1. The quantitative mechanism 8 includes a U-shaped sleeve block 18 and an I-shaped block 19. The I-shaped block 19 is located behind the U-shaped sleeve block 18 and extends to the inside of the U-shaped sleeve block 18, both side of the inside of the U-shaped sleeve block 18 are provided with an insertion slot 24 respectively, and the I-shaped block 19 extends to the inside of the insertion slot 24. The U-shaped sleeve block 18 is sleeved at the outer end of the plunger handle 4, the top of the U-shaped sleeve block 18 is provided with an indicator arrow 23, and the indicator arrow (23) is located in a front of the plunger handle (4). The back side of the I-shaped block 19 is connected to a thumb screw 20 through a thread connection, the front side of the thumb screw 20 is fixedly connected to a contact block 21, and the front side of the contact block 21 is in contact with the back side of the plunger handle 4.

The reminder mechanism 7 includes a first U-shaped seat 9 and a second U-shaped seat 10. The first U-shaped seat 9 and the second U-shaped seat 10 are respectively sleeved on both sides of the plunger handle 4. The outer sides of the first U-shaped seat 9 and the second U-shaped seat 10 are fixedly connected to a curved rubber block 15, respectively. The outer end of the curved rubber block 15 is in contact with the inner wall of the barrel 1, and the inner wall of the first U-shaped seat 9 and the inner wall of the second U-shaped seat 10 are provided with a first slot 11, respectively. The first slot 11 is fixedly connected with an elastic piece 12, and the side of the elastic piece 12 near the plunger handle 4 extends to the interior of the adjacent arc-shaped groove 5. The elastic piece in the reminder mechanism will cause some slight resistance every time it deforms and toggles, and will also emit a slight sound, which is easily felt by the doctor when injecting, and the spacing of the adjacent curved grooves 5 is fixed, so that every time the elastic toggle deforms, it represents a fixed dose of botulinum toxin is injected, and the doctor can know the real-time injection volume according to every toggle deformation, and it can also assist the doctor to control to some degree the injection speed to a certain extent.

One side of the first U-shaped seat 9 is fixedly connected to two rectangular blocks 13, one side of the second U-shaped seat 10 is provided with two rectangular slots 14, the rectangular blocks 13 are located inside the rectangular slots 14, and the first U-shaped seat 9 and the second U-shaped seat 10 are connected in an insertion connection by the rectangular blocks 13 and the rectangular slots 14. The first U-shaped seat 9 and the second U-shaped seat 10 form a middle-hollow sleeve, and the inner wall of the middle-hollow sleeve does not contact the outer wall of the plunger handle 4. The first U-shaped seat 9 and the second U-shaped seat 10 can be connected together through the rectangular blocks 13 inserted into the rectangular slots 14 to form a middle-hollow sleeve, which does not affect use and is convenient for disassembly. The inner wall of the middle-hollow sleeve does not contact the outer wall of the plunger handle 4, which can avoid interference between the two, so as to ensure the normal use of the plunger handle 4 when pushed.

The outer wall of the curved rubber block 15 is provided with an anti-slip protrusion 16, and the curved rubber block 15 is provided inside the barrel 1 in an interference fit. A limit block 17 is integrally formed at the top of each curved rubber block 15, and the quantitative mechanism 8 is located between two limit blocks 17. The elastic piece 12 is made of metal material. The anti-slip protrusion 16 can increase the friction force between the outer wall of the curved rubber block 15 and the inner wall of the barrel 1. The limit blocks 17 can not only limit the curved rubber block 15 to prevent it from moving downward inside the barrel 1, but also facilitate the removal of the reminder mechanism after use. The metal elastic dial 12 has excellent toughness, good recovery ability after deformation, and can also make some slight noises when moved.

The front side of the I-shaped block 19 is provided with a second slot 22, and the contact block 21 is located inside the second slot 22. The both sides of the I-shaped block 19 are provided with two limit balls 26, respectively, and two limit slots 25 are respectively arranged on both sides of the U-shaped sleeve block 18. The limit balls 26 are located inside the limit slots 25, and the U-shaped sleeve block 18 and the I-shaped block 19 are connected in an interference fit. The U-shaped sleeve block 18 and the I-shaped block 19 are matched and inserted together, and the limit slots 25 and limit balls 26 can make the U-shaped sleeve block 18 and the I-shaped block 19 connect in the interference fit, effectively preventing the two from being separated arbitrarily.

Working principle of the present disclosure is shown as below:

When injecting botulinum toxin through a syringe, the initial position of the quantitative mechanism 8 is pressed against the top of the barrel 1. At this time, the indicator arrow 23 points to the scale line 6 to read the initial value. Then, according to the dose needed to be injected, the quantitative mechanism 8 is moved up on the plunger handle 4, for example, by ten scale values. Before moving the quantitative mechanism 8, it is necessary to loosen the thumb screw 20 so that the contact block 21 no longer presses against the back of the plunger handle 4. At this time, the quantitative mechanism 8 can be moved. After the position of the quantitative mechanism 8 is adjusted, the user tightens the thumb screw 20 to make the contact block 21 press against the plunger handle 4 again. At this time, the position of the quantitative mechanism 8 on the plunger handle 4 is fixed, and then push the plunger handle 4 for injection. When the quantitative mechanism 8 is moved down with the plunger handle 4 until it reaches the top of the barrel 1, the quantitative mechanism 8 cannot be moved down any further, and the plunger handle 4 cannot be moved down any further as well, so as to achieve the goal of precise dose injection.

When plunger handle 4 is pushed to move down for the injection, as the plunger handle 4 is moved down, the elastic piece 12 inserted into the corresponding arc-shaped groove 5 will gradually bend and then enter an adjacent arc-shaped groove 5. During this period, each movement of the elastic piece 12 indicates that a certain amount of botulinum toxin has been injected. Doctors can use this function to clearly know the real-time injection amount during the injection period, and it is also convenient to control the injection speed.

The reminder mechanism 7 and the quantitative mechanism 8 can be disassembled for recycling. The reminder mechanism 7 can pick up the limit block 17 and pull out the two curved rubber blocks 15 from the barrel 1 during disassembly. After pulling them out, the user just separates the first U-shaped seat and the second first U-shaped seat 10. The quantitative mechanism 8 only needs to loosen the thumb screw 20 during disassembly, then lift or press the I-shaped block 19 up or down to separate the U-shaped sleeve block 18 from the I-shaped block 19. Then, the U-shaped sleeve block 18 can be removed from the plunger handle 4. When using it again, the user just need to reverse the above steps to install the reminder mechanism 7 and the quantitative mechanism 8.

What is claimed is:

1. A precise dose syringe for medical botulinum toxin, comprising a barrel (1), a needle (2), a plunger (3), and a plunger handle (4), wherein the needle (2) is inserted and connected to a tip at a bottom of the barrel (1), the plunger (3) is located inside the barrel (1), the plunger handle (4) is fixedly connected to a top of the plunger (3), and the plunger handle (4) is located inside the barrel (1) and extends to a top of the barrel (1); a cross-section of the plunger handle (4) is square, a plurality of arc-shaped grooves (5) are provided on both sides of the plunger handle (4), and a front side of the plunger handle (4) is provided with a scale line (6); an outer side of the plunger handle (4) is sleeved with a reminder mechanism (7) and a quantitative mechanism (8), the reminder mechanism (7) is located inside the barrel (1) and extends out of the top of the barrel (1), and the quantitative mechanism (8) is located above the barrel (1); the quantitative mechanism (8) comprises a U-shaped sleeve block (18) and an I-shaped block (19), the I-shaped block (19) is located behind the U-shaped sleeve block (18) and extends to an inside of the U-shaped sleeve block (18), both side of the inside of the U-shaped sleeve block (18) are provided with an insertion slot (24) respectively, the I-shaped block (19) extends to an inside of the insertion slot (24), the U-shaped sleeve block (18) is sleeved at an outer end of the plunger handle (4), a top of the U-shaped sleeve block (18) is provided with an indicator arrow (23), the indicator arrow (23) is located in a front of the plunger handle (4), a back side of the I-shaped block (19) is connected to a thumb screw (20) through a thread connection, a front side of the thumb screw (20) is fixedly connected to a contact block (21), and a front side of the contact block (21) is in contact with a back side of the plunger handle (4);

the reminder mechanism (7) comprises a first U-shaped seat (9) and a second U-shaped seat (10), wherein the first U-shaped seat (9) and the second U-shaped seat (10) are respectively sleeved on both sides of the plunger handle (4), outer sides of the first U-shaped seat (9) and the second U-shaped seat (10) are fixedly connected to a curved rubber block (15) respectively, an outer end of the curved rubber block (15) is in contact with an inner wall of the barrel (1), an inner wall of the first U-shaped seat (9) and an inner wall of the second U-shaped seat (10) are provided with a first slot (11) respectively, the first slot (11) is fixedly connected with an elastic piece (12), and a side of the elastic piece (12) near the plunger handle (4) extends to an interior of the adjacent arc-shaped groove (5); and a front side of the I-shaped block (19) is provided with a second slot (22), and the contact block (21) is located inside the second slot (22).

2. The medical precise dose syringe for botulinum toxin according to claim 1, wherein one side of the first U-shaped seat (9) is fixedly connected to two rectangular blocks (13), one side of the second U-shaped seat (10) is provided with two rectangular slots (14), the two rectangular blocks (13) are located inside the two rectangular slots (14), and the first U-shaped seat (9) and the second U-shaped seat (10) are connected in an insertion connection by the rectangular blocks (13) and the rectangular slots (14).

3. The medical precise dose syringe for botulinum toxin according to claim 1, wherein the first U-shaped seat (9) and the second U-shaped seat (10) form a middle-hollow sleeve, and an inner wall of the middle-hollow sleeve does not contact an outer wall of the plunger handle (4).

4. The medical precise dose syringe for botulinum toxin according to claim 1, wherein an outer wall of the curved rubber block (15) is provided with an anti-slip protrusion (16), and the curved rubber block (15) is provided inside the barrel (1) in an interference fit.

5. The medical precise dose syringe for botulinum toxin according to claim 1, wherein a limit block (17) is integrally formed at a top of each curved rubber block (15), and the quantitative mechanism (8) is located between two limit blocks (17).

6. The medical precise dose syringe for botulinum toxin according to claim 1, wherein the elastic piece (12) is made of metal material.

7. The medical precise dose syringe for botulinum toxin according to claim 1, wherein both sides of the I-shaped block (19) are provided with two limit balls (26) respectively, two limit slots (25) are respectively arranged on both sides of the U-shaped sleeve block (18), the limit balls (26) are located inside the limit slots (25), and the U-shaped sleeve block (18) and the I-shaped block (19) are connected in an interference fit.

\* \* \* \* \*